United States Patent [19]

Brandes et al.

[11] 4,237,325

[45] Dec. 2, 1980

[54] METHOD OF CONDUCTING REACTIONS IN A TRICKLE-TYPE REACTOR

[75] Inventors: Günter Brandes, Hamburg; Johannes Wöllner, Kapellen Krs. Moers; Wilhelm Neier; Werner Webers, both of, Orsoy, all of Fed. Rep. of Germany

[73] Assignee: Deutsche Texaco Aktiengesellschaft, Hamburg, Fed. Rep. of Germany

[21] Appl. No.: 953,507

[22] Filed: Oct. 23, 1978

Related U.S. Application Data

[62] Division of Ser. No. 545,641, Jan. 30, 1975.

[30] Foreign Application Priority Data

Jan. 30, 1974 [DE] Fed. Rep. of Germany ....... 2404329

[51] Int. Cl.$^3$ ............................................ C07C 29/17
[52] U.S. Cl. .................................................. 568/896
[58] Field of Search ................ 260/513; 568/895, 896

[56] References Cited

U.S. PATENT DOCUMENTS

4,003,952  1/1977  Foster et al. ........................ 568/895

OTHER PUBLICATIONS

Hanika et al., Coll. Cyech Comm., vol. 39, pp. 210–215 (1974).
Satterfield A.I.Ch.E. J., vol 21(2), pp. 209–228 (1975).

*Primary Examiner*—Natalie Trousof
*Assistant Examiner*—James H. Reame
*Attorney, Agent, or Firm*—Carl G. Ries; Robert A. Kulason; Robert Knox, Jr.

[57] ABSTRACT

Trickle-type fixed-bed catalytic reactions are improved, prior to starting or resuming an on-stream period, by purging air from the catalyst bed and reaction zone by downward flow of an inert gas therethrough, flooding the purged reaction zone by flowing a liquid upwardly through the catalyst bed to cover same, then removing the liquid and instituting the on-stream period by introducing gaseous and liquid reactants at the upper end of the catalyst bed to flow downwardly therethrough.

10 Claims, No Drawings

METHOD OF CONDUCTING REACTIONS IN A TRICKLE-TYPE REACTOR

This is a division, of application Ser. No. 545,641 filed Jan. 30, 1975.

This invention relates to the conducting of continuous reactions at elevated temperature and pressure in a trickle-type reactor using a fixed-bed catalyst traversed by gaseous and liquid reactants, particularly in downward cocurrent flow.

Various methods are known for carrying out the above-described type of reactions. For example, German Auslegeschrift No. 1 291 729 discloses the preparation of lower alcohols and ethers by direct hydration of lower olefins in a reactor filled with particles of a sulfonated synthetic resin catalyst in a fixed bed and charged with liquid water and gaseous olefin, especially propylene, at temperatures of 110° to 170° C. and under a pressure of from 60 to 120 atmospheres gauge, advantageously in downward cocurrent flow direction. Other embodiments of this known procedure are disclosed, for example, in German Offenlegungsschriften Nos. 2 147 737, 2 147 738 or 2 147 739.

A further method of this type is disclosed in German Pat. No. 1 260 454, which method is used for preparing higher carbonyl compounds by condensation of lower carbonyl compounds and simultaneous hydrogenation of the unsaturated intermediate product. In this method, the fixed-bed catalyst consists of a strongly acid cation exchange resin which comprises a hydrogenating metal.

In practice, when such reactions are carried out in trickle-type reactors, frequent difficulties occur when the reactor is filled with the catalyst and put into operation, or, when the reaction is interrupted and subsequently operation is resumed. As a rule, the catalyst suspended in a suitable fluid—preferably a liquid reactant—is introduced or slurried into the reactor until the catalyst bed has attained the desired depth in the reactor. After the reactor has been filled with catalyst, the remaining air in the reactor system (in the reactor top and bottom sections as well as between the catalyst grains) must be displaced and removed. This is effected by flushing the reactor with an inert gas or with the gaseous component of the intended reaction.

In case of relatively coarse catalyst particles having an average particle, or grain, diameter of, for example 4 mm or more, these displacement measures taken in reactor systems do not present any difficulties, but they are frequently ineffective and may even cause damage in the case of fine-grained catalysts where the average catalyst particle size is below 2 or perhaps 1.5 mm. If, for example, a fine-grained catalyst is slurried into the reactor, and an attempt is made to displace the trapped air by flushing the reactor (in upward direction), the air underneath the catalyst bed will push the moist catalyst like a piston and may destroy interior installations, such as intermediate trays and the like, in larger reactors. If, however, the entrapped air is displaced by introducing an (inert) gas at the top of the reactor, this will result in simultaneously displacing the liquid used for slurrying the catalyst as a considerable portion of said liquid is retained by capillary forces in the fine-grained catalyst bed.

It has been shown that a fine-grained catalyst bed which has been freed from air by flushing with inert gas, often no longer is capable of ensuring a uniform distribution of the liquid reactant in the catalyst bed during the subsequent reaction. In fact, zones are formed within the catalyst bed, which are not or are insufficiently traversed by the trickling fluid. This irregular distribution of the liquid often results in the formation of hot spots in the catalyst bed, and the space-time yield and, frequently, the selectivity of the reaction as well as the effective lifetime of the catalyst are seriously affected. It has been found, surprisingly, that these difficulties and the formation of "dry" zones cannot be remedied by spraying the inert gas-flushed catalyst bed with the liquid reactant prior to putting the reactor on-stream. Similar troubles and difficulties are encountered when, after an interruption, the continuous reaction process is to be resumed in such a reactor, even if the reactor was out of operation for only a few hours.

Therefore, it is the object of this invention to provide a method for executing the type of reactions mentioned above which method does not suffer from the described disadvantages and guarantees substantially uniform contact of the catalyst bed with the reactants subsequent to filling fresh catalyst into the reactor or after an interruption of operations.

Our invention provides a process for carrying out reactions between gaseous and liquid reactants where in an on-stream period, the reactants pass in contact with a fixed bed of particulate catalyst in a reaction zone which process comprises prior to instituting the on-stream period removing air from said reaction zone by passing a gas devoid of free oxygen downwardly through said reaction zone and said catalyst bed, interrupting the flow of said gas and introducing a liquid to flow upwardly through said catalyst bed and cover same and then removing said liquid from said reaction zone and substantially simultaneously introducing said gaseous and liquid reactants into said reaction zone to flow downwardly through said catalyst bed and instituting the on-stream period.

In a more specific embodiment these objects are achieved by first filling the reactor in a manner known per se with a fine-grained catalyst in the form of a suspension or slurry to form a catalyst fixed bed of predetermined depth, then purging the fixed bed with an inert gas in downward direction until substantially all of the air has been displaced from the reaction chamber then flooding the fixed-bed catalyst in upward direction with a suitable liquid medium using conveniently the liquid reactant, and, then, lowering the liquid level in the fixed-bed catalyst by introducing a gas such as an inert gas or more conveniently the gaseous reactant while continuously spraying the bed with the liquid reactant, and starting the reaction.

The method of the invention makes it possible to carry out exothermic reaction processes in trickle columns using very fine granular catalyst with a mean grain size of less than about 2, or even less than about 1.5 mm, in an improved manner. Conveniently, the catalyst bed is purged with about 3 standard liters of inert gas per $cm^2$ of bed cross-sectional area per hour and then liquid is introduced upwardly at a rate of from about 1 to 3 $m^3$ of liquid per $m^2$ of bed cross-sectional area per hour. Although higher flood rates are possible, they may result in incomplete wetting of the catalyst surface. Advantageously the catalyst bed is flooded under elevated pressure, this measure favoring the wetting of "dry" spots in the fixed bed. The flooding under superatmospheric pressures does not usually involve extra costs, since with a new charge being fed to the reactor, a pressure test is ordinarily carried out.

The term "inert gas" when used to describe the purging medium used in the process of our invention is intended to mean a gas which is substantially devoid of free oxygen. Examples of such gases are nitrogen, hydrogen, methane and the like and mixtures thereof.

The method of this invention is described in greater detail in the examples and comparative examples below, describing the production of lower alcohols, specifically isopropyl alcohol.

EXAMPLE 1

A reactor of 9 m height and 280 mm inside diameter was filled with the aqueous suspension of 500 liters of a strongly acid cation exchange resin "Amberlite 252" having a grain size of from 0.3 to 1.2 mm. It may be purchased from Rohm & Haas company and is a macroporous sulfonated styrene/divinyl benzene copolymer with about 12% divinyl benzene which acts as cross-linking agent. The bulk density is about 800 grs/liter and the exchange capacity is about 1.25 equivalents per liter. The specific surface is about 39–40 $m^2$/gr., the pore volume 0.183 $cm^3$/gr. The density in dry condition amounts to 390–400 grs. per liter. The air present in the reactor was displaced, only by flushing with nitrogen.

Subsequently, the catalyst was sprayed with 8.5 $m^3$ of water per $m^2$ cross-sectional area per hour and reaction conditions were adjusted to a propylene pressure of 100 atmospheres gauge and a temperature of 135° C. 742 kg of propylene* per $m^2$ of reactor cross-sectional area per hour was added, i.e., a propylene charge of 2.0 moles per liter of catalyst volume per hour. Catalyst performance attained 1.5 moles of isopropyl alcohol (IPA) per liter of catalyst volume per hour and a selectivity for IPA of from 90 to 92 percent. The by-products formed consisted of about 8 to 10 percent of diisopropyl ether and less than 0.2 percent of propylene polymers.

* a $C_3$ mixture containing 92% propylene

When the distribution of the temperature in the catalyst bed was measured, locally confined excess temperatures up to about 180° C. were found to have occurred, especially in the upper reactor section. When the reactor was emptied, several zones of from 5 to 15 cm thickness were found in the fixed bed where the catalyst had the appearance of a tarry cake-like mass.

EXAMPLE 2

The reactor described in Example 1 was filled with the same catalyst in the manner indicated in that example and entrapped air and water present in the grain interstices were removed therefrom by introducing 3 liters of nitrogen per $cm^2$ per hour at the top of the reactor. Thereafter, the reactor was filled from the bottom with water at a flooding rate of 120 l/hr. and the water pressure was adjusted to about 100 atmospheres gauge. Upon relieving the water pressure, the liquid level in the reactor was lowered under spraying with 8.5 $m^3/m^2$/hr. of water and introducing propylene at the top of the reactor, and the reaction conditions were adjusted as described in Example 1 (pressure: 100 atmospheres gauge; temperature: 135° C.). This time, in order to attain once more a propylene conversion of 75 percent, 3.18 mols of 92% propylene per liter of catalyst per hour was charged at the reactor top. Catalyst performance attained was 2.2 moles of IPA/liter of catalyst volume per hour and a selectivity for IPA liter of catalyst volume per hour and a selectivity for IPA of 98.5 percent. No polymers were found.

The temperature distribution in the reactor was shown to be uniform, ranging at 135°±3° C. across the longitudinal and the cross-sectional reactor profiles.

EXAMPLE 3

The continuous production of IPA according to Example 2 was interrupted for 48 hours.

Before resuming IPA production the reactor was flooded with water according to the procedure of Example 2, and the water level, under spraying of the catalyst with water, lowered by introducing propylene. Then the reactor was adjusted to the same reaction conditions (propylene pressure of 100 atmospheres gauge, temperature of 135° C.).

The catalyst performance (2.2 moles IPA/l/hr.), selectivity and temperature distribution attained after adjusting the equilibria were the same as before the interruption.

EXAMPLE 4

The continuous test run described in Examples 2 and 3 was interrupted for 48 hours.

In order to resume operations, the catalyst first was sprayed only with 8.5 $m^3$ of water per $m^2$ of reactor cross-sectional area per hour, and then the reaction conditions in the reactor were adjusted as heretofore described (propylene pressure of about 100 atmospheres gauge temperature of 135° C.). The catalyst performance was measured to be 1.7 moles of IPA per liter of catalyst volume per hour.

Temperature measurements along the longitudinal and cross-sectional reactor profiles showed temperature to have risen by 15° to 20° C. above normal at some spots, said excess temperatures disappearing gradually only after several days. IPA selectivity during this time was at 94 percent.

As shown in the examples, maximum yields and selectivities and uniform temperature distribution are attained when the fixed-bed catalyst, which is free from air or from which the air has been removed is flooded prior to starting or re-starting the reaction, the flooding step being conveniently conducted under the pressure employed for the reaction, and then the liquid level is lowered under spraying while introducing the gaseous reactant. The superior results attained by following this procedure are not achieved if the flooding step is omitted or if the reactor system is purged with only inert gas or the gaseous reactant to displace the air therefrom even if the fixed bed is sprayed in the aforementioned manner. The successful procedure according to the invention seems to be attributable primarily to flooding the fixed-bed catalyst conveniently under elevated pressure, prior to the beginning or the resumption of the reaction. The flooding of the fixed-bed catalyst should not, or not appreciably, change the location of the catalyst particles. Movement of the particles is not required nor intended.

If the reaction is carried out with reactants capable of reacting with the catalyst as may be the case with strongly acid cation exchange resin catalyst employed for reactions of olefins, it is an advantage to displace any olefin still present in the reactor, after it has been closed down, by an inert gas or a suitable liquid, e.g., water. The chosen material should be one in which the catalyst does not swell substantially while the unit is idle. Under this condition, it may be an advantage to interrupt the reaction by stopping the addition of olefin, flooding the reactor with water or some other suitable liquid medium and leaving it in this condition until resuming operations. This may be done by lowering the liquid level in the reactor by introducing olefin and simultaneously spraying the fixed-bed catalyst with the liquid reactant. This simple procedure precludes a reduction in catalyst activity during the idle time of the unit.

Various modifications of the invention as hereinbefore set forth may be made without departing from the spirit and scope thereof, and therefore, only such limitations should be made as are indicated in the appended claims.

The embodiments of the invention in which an exclusive property or privilege is claimed are defined as follows:

1. In a process for carrying out a hydration reaction between a gaseous olefin and water where in an on-stream period the reactants pass downwardly in contact with a fixed bed of particulate olefin hydration catalyst having an average particle size no greater than about 2 mm in a trickle-type reaction zone, the improvement which comprises prior to instituting the on-stream period removing air from said reaction zone by passing a gas devoid of free oxygen downwardly through said reaction zone and said catalyst bed, interrupting the flow of said gas devoid of free oxygen and flooding the reaction zone by introducing a liquid to flow upwardly through said catalyst bed and cover same and then removing said liquid from said reaction zone and substantially simultaneously introducing said gaseous olefin and water into said reaction zone to flow downwardly through said catalyst bed, under hydration conditions, thereby instituting the on-stream period.

2. The process of claim 1 in which the gaseous olefin is propylene.

3. The process of claim 1 in which to flood the reaction zone, water is passed upwardly at a rate between about 1 and 3 $m^3$ of water per $m^2$ of bed cross sectional area per hour and the gas devoid oxygen is said olefin reactant.

4. The process of claim 3 which the gaseous olefin comprises propylene, the gas devoid of oxygen comprises propylene and the product comprises isopropyl alcohol.

5. The process of claim 3 in which the flooding by the water is conducted at substantially the same pressure as the hydration reaction.

6. The process of claim 1 in which the gas devoid of oxygen is nitrogen.

7. The process of claim 1 in which the gas devoid of oxygen is hydrogen.

8. The process of claim 1 in which the gas devoid of oxygen is said gaseous reactant.

9. The process of claim 1 in which the gas devoid of oxygen is passed downwardly through the catalyst bed at a rate of about 3 standard liter per $cm^2$ of bed cross-sectional area per hour.

10. The process of claim 1 in which the particles have an average size no greater than 1.5 mm.

* * * * *